United States Patent

Hatanaka

(10) Patent No.: US 6,410,612 B1
(45) Date of Patent: Jun. 25, 2002

(54) DENTURE REBASES

(75) Inventor: Kenji Hatanaka, Okayama-ken (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 09/518,137

(22) Filed: Mar. 3, 2000

(30) Foreign Application Priority Data

Mar. 3, 1999 (JP) .......................................... 11-054847

(51) Int. Cl.[7] .............................................. A61K 6/083
(52) U.S. Cl. ....................... 523/115; 523/113; 523/118; 433/228.1; 433/526; 433/245; 433/246
(58) Field of Search ................................ 523/109, 113, 523/115, 116, 117, 118, 120; 433/238.1; 526/245, 246

(56) References Cited

U.S. PATENT DOCUMENTS 5,061,184 A * 10/1991 Yamazaki et al. ....... 433/228.1

FOREIGN PATENT DOCUMENTS

| EP | 0 149 924 | 7/1985 |
|----|-----------|--------|
| EP | 0 211 408 | 2/1987 |
| EP | 0 358 195 | 3/1990 |
| EP | 0 373 385 | 6/1990 |
| JP | 62-033110 | 2/1987 |

OTHER PUBLICATIONS

Yohichiro Ohe, et al. *Study on Visible–light Curing Soft Resins Consisting of Fluoropolymers* The Journal of the Japanese Society for Dental Materials and Devices, vol. 9, No. 2, Mar. 1990.

Yung–chan Kuo, et al. *Studies on Dental Acrylic Resins Containing 2,2,2,—Trifluoroethyl Methacrylate*; Journal of the Japanese Society for Dental Materials and Devices, vol. 2, No. 1, Jan. 1983.

* cited by examiner

*Primary Examiner*—Peter Szekely
(74) *Attorney, Agent, or Firm*—Oblon, Spivak, McClelland, Maier & Neustadt, P.C.

(57) ABSTRACT

A denture rebase is provided, which includes:

(a) an acrylic resin;

(b) a fluoro(meth)acrylate having the formula (I):

$$CH_2=C(R^1)COO-R^2-Rf \qquad (I)$$

wherein $R^1$ represents a hydrogen atom or a methyl group; $R^2$ represents an alkylene group; Rf represents a perfluoro alkyl group; $R^2$+Rf has 4 to 10 carbon atoms in total, and wherein at least 50% of all atoms bonded to said carbon atoms constituting $R^2$+Rf are fluorine atoms;

(c) a polyfunctional (meth)acrylate; and (d) a polymerization initiator.

The denture rebase is free from the serious problems associated with conventional denture rebases. The denture rebase resists discoloration and staining, and it is resistant to the absorption of odorous substances and water. It has good contamination resistance, and its cured product is tough.

20 Claims, No Drawings

DENTURE REBASES

BACKGROUND OF THE INVENTION

1. Field of the Invention

The present invention relates to denture rebases.

2. Description of the Related Art

Acrylic, polysulfone or polycarbonate dentures are typically used in dental treatment for the aged and those who have lost their teeth. In general, however, ridge resorption is often remarkable in cases with dentures. In such cases, the alveolar bone will often "cave in" as the oral mucous membrane that helps to cushion the teeth becomes poor and also as the jawbone is resorbed. Accordingly, over time, the fit of even well-made dentures will progressively become worse.

In cases where the denture has failed to fit well within the oral cavity, a denture rebase is generally applied. A denture rebase reconstitutes the surface of the denture that faces the oral mucous membrane; and the thus-reconstructed denture fits better in the mouth. These denture rebases are used as follows: an un-polymerized and un-cured denture rebase (i.e., one that is pasty) is applied to the surface of the ill-fitting denture that faces the oral mucous membrane, then the denture, together with the applied rebase on its surface is returned to the oral cavity of the patient, and the upper and lower teeth of the patient are made to occlude such that the denture is in good contact with the oral mucous membrane and such that the rebase on the denture is impressed with the surface profile of the oral mucous membrane, and thereafter the rebase is polymerized and cured. In this treatment, the rebase can be directly polymerized and cured while it is still in the oral cavity or, alternatively, the rebase may be taken out after having been once impressed with the surface profile of the oral mucous membrane, and then polymerized and cured outside the oral cavity.

However, compared to the dentures themselves, conventional denture rebases are problematic in that they are readily discolored, they absorb odorous substances and water, and they are easily contaminated and stained if they remain in the oral cavity for a long time. In addition, the care of such dentures is often more difficult for aged persons, and dentures relined with such conventional rebases are easily contaminated and stained with use, which adds to the worsening of the dental condition of the patient. Another problem with conventional rebases is that they are often painful to the patients who undergo dental treatment with them. This is because of the irritation caused to the oral mucous membrane during contact with the rebase before polymerization.

To prevent denture rebases from being contaminated and stained, fluorine-containing dental materials have been proposed. Such materials typically contain (meth)acrylate monomers having fluorine atoms. For example, Japanese Patent Laid-Open No. 33110/1987 discloses a dental composition containing an acrylate polymer having a fluorine atom in its α-position. The composition gives a dental material having high mechanical strength. However, this dental material is undesirably subject to discoloration, its staining resistance is not satisfactory, and it absorbs odorous substances and water while in the oral cavity. In addition, even though the dental material has high mechanical strength, it is not tough and its cured product is hard and brittle.

In *Dental Materials and Appliances*, Vol. 9, No. 2, pp. 257–264 (1990), a composition for soft denture rebases is disclosed, which contains, as the polymer ingredient of fluororubber, a vinylidene fluoride-hexafluoropropylene copolymer or a vinylidene fluoride-tetrafluoroethylene-hexafluoropropylene copolymer, and, as the monomer ingredient, a fluoro(meth)acrylate having 2 to 5 side-chain carbons. As compared with conventional soft rebases, those prepared by polymerizing and curing the composition disclosed therein are better since they absorb a reduced amount of water and release a reduced amount of the constituent monomer; but they are still unsatisfactory since they are readily discolored and stained, and they absorb odors in the mouth.

In *Dental Materials and Appliances*, Vol. 2, No. 1, pp. 50–57 (1983), a dental resin is disclosed that contains, as the polymer component, polymethyl methacrylate and, as the monomer component, 2,2,2-trifluoroethyl methacrylate. The primary advantage of this resin composition is that the amount of protein that adheres to it is reduced in some degree. However, its effect is not satisfactory and, in addition, the dental resin is easily discolored and stained, and it absorbs water and odors while used in the mouth.

In the conventional methods mentioned above, it is difficult to obtain denture rebases having satisfactory discoloration and staining resistance, odor absorption resistance and water absorption resistance. In addition, the polymerized and cured products of the conventional materials noted above are undesirably brittle though being hard. Moreover, still another problem is that the convention denture rebases irritate the oral mucous membrane when, prior to their being polymerized, they are kept in contact with the oral mucous membrane while being impressed with the surface profile thereof.

Accordingly, conventional denture rebases have the serious problem in that they are easily contaminated and stained as compared with the dentures themselves. Dental materials containing a fluoro(meth)acrylate have been used, but which are still defective in that their contamination and staining resistance is not satisfactory, and they become brittle after curing.

SUMMARY OF THE INVENTION

Accordingly, one object of the invention is to provide denture rebases having good contamination and staining resistance.

Another object of the invention is to provide denture rebases that remain tough after being cured.

Another object of the invention is to provide denture rebases that do not irritate the oral mucous membrane while being impressed with the surface profile of the oral mucous membrane.

Another object of the invention is to provide denture rebases that do not cause pain to the patients who undergo dental treatment with them.

These and other objects have been attained by the present invention, the first embodiment of which provides a denture rebase that includes:

(a) an acrylic resin;

(b) a fluoro(meth)acrylate having the formula (I):

$$CH_2=C(R^1)COO-R^2-Rf \qquad (I)$$

wherein $R^1$ represents a hydrogen atom or a methyl group; $R^2$ represents an alkylene group; Rf represents a perfluoro alkyl group; $R^2$+Rf has 4 to 10 carbon atoms in total, and wherein at least 50% of all atoms bonded to said carbon atoms constituting $R^2$+Rf are fluorine atoms;

(c) a polyfinctional (meth)acrylate; and (d) a polymerization initiator.

Another embodiment of the invention provides a dental rebase, that includes the cured reaction product of the above-noted (a), (b), (c) and (d).

Another embodiment of the invention provides a method of making the denture rebase, that includes combining the above-noted (a), (b), (c) and (d).

Another embodiment of the invention provides a method rebasing a denture. that includes applying to a surface of a denture the above denture rebase composition.

Another embodiment of the invention provides a two-package powder/liquid composition, which includes:

a powder package, including:
  (a) an acrylic resin powder, and
  (d') a peroxide; and a liquid package, including:
  (b) a fluoro(meth)acrylate having the formula (I):

(I)

wherein $R^1$ represents a hydrogen atom or a methyl group; $R^2$ represents an alkylene group; Rf represents a perfluoro alkyl group; $R^2$+Rf has 4 to 10 carbon atoms in total, and wherein at least 50% of all atoms bonded to said carbon atoms constituting $R^2$+Rf are fluorine atoms, (c) a polyftnctional (meth)acrylate, and (d") a tertiary amine;

wherein when (d') and (d") are combined, a polymerization initiator (d), is formed.

Another embodiment of the invention provides a method for making a dental rebase, that includes combining the above powder and liquid packages.

DESCRIPTION OF THE PREFERRED EMBODIMENTS

Various other objects, features and attendant advantages of the present invention will be more fully appreciated as the same becomes better understood from the following detailed description of the preferred embodiments of the invention.

In the denture rebase of the invention, the fluoro(meth) acrylate (b) of formula (I) is believed to participate in improving the discoloration and staining resistance of the denture rebase. The fluoro(meth)acrylate (b) in the composition is believed to be effective for preventing the composition from irritating the oral mucous membrane when the uncured composition is kept in contact with the oral mucous membrane when being impressed with the surface profile of the membrane. In formula (I), $R^2$ represents an alkylene group, and Rf represents a perfluoroalkyl group. The alkylene group and the perfluoroalkyl group may independently be linear, branched or cyclic. The hydrogen atoms thereon may be partially substituted with hydroxyl groups. Preferably, in order to improve the discoloration and staining resistance of the cured composition and to prevent the non-cured composition from irritating the oral mucous membrane, $R^2$+Rf in formula (I) for the component (b) must have at least 4 carbon atoms in total, but preferably at least 6 carbon atoms, and the fluorine atoms bonding to the carbon atoms that constitute $R^2$+Rf must account for at least 50% of all the atoms bonding thereto. With the increase in the number of the carbon atoms constituting $R^2$+Rf, the discoloration and staining resistance of the cured composition increases and the non-cured composition does not irritates the oral mucous membrane, so long as the fluorine atoms bonding to the carbon atoms that constitute $R^2$+Rf account for at least 50% of all the atoms bonding thereto. However, increasing the number of the carbon atoms constituting $R^2$+Rf above 10 reduces the toughness of the polymerized and cured composition.

The polyftuctional (meth)acrylate (c) in the composition is believed to improve the toughness of the cured composition to some degree. Too much of the monomer (c) in the composition is less preferred, since it may as reduce the discoloration and staining resistance of the cured composition. From this viewpoint, the number of carbon atoms constituting $R^2$+Rf in the component (b) must be at most 10, and it must fall between 4 and 10.

The fluoro(meth)acrylate (b) is believed to be effective for preventing the cured composition from being discolored and stained and for preventing the non-cured composition from irritating the oral mucous membrane, but if the composition contains only the component (b) as the monomer component, its polymerized and cured product could not have a crosslinked structure and it is difficult to prevent odorous substances and water from penetrating into the cured composition. Therefore, for preventing the cured composition from absorbing odorous substances and water, adding a polyfuictional (meth)acrylate to the composition is believed to be more effective. The amount of the monomer (c) to be in the composition may fall between 0.1 and 20% by weight, but preferably between 2 and 15% by weight. If the monomer (c) amount is smaller than 0.1% by weight, the cured composition will still absorb water and odorous substances. But if the amount of monomer (c) is larger than 20% by weight, the discoloration and staining resistance of the cured composition will decrease. Preferable examples of monomer (c) include at least one monomer of alkylene glycol di(meth)acrylates in which the alkylene group between the two (meth)acryloyl groups has from 3 to 20 carbon atoms (the alkylene group may be linear, branched or cyclic), which is believed to be more effective for preventing water and odorous substances from being absorbed by the cured composition and for improving the toughness of the cured composition.

The composition of the invention includes an acrylic resin as the polymer component, a fluoro(meth)acrylate of formula (I) and a polyfunctional (meth)acrylate as the monomer components, and a polymerization initiator. In this, the acrylic resin is indispensable for the matrix of denture rebases; and the fluoro(meth)acrylate and the polyfunctional (meth)acrylate are particularly suitable for solving the problems with conventional rebases which are discolored and stained and absorb water and odorous substances to a great extent.

Preferably, the acrylic resin in the denture rebase of the invention is a polymer having (meth)acrylate units of at least one type and other monomer units capable of copolymerizing with them. For example, the methacrylate may include any one or more of methyl methacrylate, ethyl methacrylate, butyl methacrylate, pentyl methacrylate. cyclohexyl methacrylate, etc.; and the acrylate includes any one or more of methyl acrylate. ethyl acrylate, butyl acrylate, 2-ethylhexyl acrylate, cyclohexyl acrylate, benzyl acrylate, etc. These (meth)acrylates may be used either singly or as combined, for constituting the copolymer.

Other preferred monomers capable of copolymerizing with such (meth)acrylates include, for example, dienic compounds such as 1,3-butadiene, 2,3-dimethylbutadiene, isoprene, etc.; aromatic vinyl compounds such as styrene, vinyltoluene, α-methylstyrene, etc.; N-substituted maleimides such as N-cyclohexylmaleimide, N-O-chlorophenylmaleimide, N-tert-butylmaleimide, etc.; vinyl cyanide compounds such as acrylonitrile, methacrylonitrile, etc. These comonomers may be used either singly or as combined, for constituting the copolymer.

Crosslinkable monomers are also usable as the comonomers. For example, they are preferably polyfinctional monomers, including allyl methacrylate, allyl acrylate, triallyl cyanurate, allyl cinnamate, allyl sorbate, diallyl maleate, diallyl phthalate, triallyl trimellitate, diallyl fumarate, ethylene glycol di(meth)acrylate, polyethylene glycol di(meth)acrylate, divinylbenzene, 1,3-butylene glycol di(meth)acrylate, 1,6-hexanediol di(meth)acrylate, etc. These comonomers may be used either singly or as combined, for constituting the copolymer.

Of the components constituting the acrylic resin noted above, preferred are polymethyl methacrylates, polyethyl methacrylates and polymethyl methacrylate-polyethyl methacrylate copolymers in view of the mechanical strength and the transparency of the polymerized and cured composition. Especially preferred are polyethyl methacrylates, polymethyl methacrylate-polyethyl methacrylate copolymers, or mixtures of these polymers with other polymers, as they are highly compatible with the monomer components (b) and (c) to be in the composition.

For further improving the mechanical strength of the polymerized and cured composition, the acrylic resin in the composition may be combined with a resin composite having a core/shell resin and/or a (meth)acrylic resin. The core/shell resin is preferably a multi-layered resin having at least one hard layer and at least one soft layer and containing an outermost hard layer. In this, the hard layer is of a resin having Tg of not lower than 40° C. preferably 50° C., more preferably 60° C.; and the soft layer is of a resin having Tg of lower than 20° C., preferably 15° C., more preferably 10° C. The (meth)acrylic resin to form the resin composite together with the core/shell resin preferably has Tg of not lower than 40° C. preferably 50° C., more preferably 60° C. The core/shell resin and the (meth)acrylic resin to form the resin composite together with the core/shell resin are prepared from monomers for acrylic resin such as those mentioned hereinabove, while being so controlled that they could have the intended Tg.

The acrylic resin to be in the composition of the invention preferably has a molecular weight of from 10,000 to 1,000,000, more preferably from 100,000 to 700,000. If the molecular weight of the resin is smaller than 10,000, the polymerized and cured composition could not be tough; but if larger than 1,000,000, the solubility of the acrylic resin in the fluoro(meth)acrylate will be low and the composition will be difficult to handle.

The denture rebase of the invention may be in two different package forms. One is a two-package product composed of a powder package of an acrylic resin powder and a liquid package containing, as the essential ingredients, the specific fluoro(meth)acrylate and a polyfimctional (meth)acrylate; and the other is a one or two -package product of a paste as prepared by mixing an acrylic resin with a liquid that contains, as the essential ingredients, the specific fluoro(meth)acrylate and a polyfunctional (meth) acrylate.

For the powdery acrylic resin for use in the invention, the preferred range of its mean particle size may differ, depending on the package forms of the composition. Concretely, in the two-package product composed of a powder package of an acrylic resin powder and a liquid package containing, as the essential ingredients, the specific fluoro(meth)acrylate and a polyfunctional (meth)acrylate, the two are mixed to give a paste before use, and the resulting paste is applied to the oral cavity. After mixed, the powder component is swollen or dissolved in the liquid component, and the viscosity of the resulting mixture paste shall increase with the lapse of time. The time-dependent increase in the viscosity of the paste depends on the particle size of the acrylic resin powder. Therefore, the mean particle size of the acrylic resin powder preferably falls between 1 and 150 $\mu$m, more preferably between 10 and 100 $\mu$m.

If its mean particle size is smaller than 1 $\mu$m, the acrylic resin powder will dissolve too rapidly in the monomer component, and the viscosity of the resulting paste composition will thereby increase too rapidly. If so, the paste composition could not be impressed well with the surface profile of the oral mucous membrane in the oral cavity. On the other hand, if its mean particle size is larger than 150 $\mu$m, the acrylic resin powder could not well dissolve in the monomer component to increase the viscosity of the resulting composition. If so, the composition could not be pasty. What is more, if its mean particle size is smaller than 1 $\mu$m, the acrylic resin powder easily scatters, and the composition containing such a scattering fine powder will be difficult to handle. In the other one-package product of a paste composition to be prepared by mixing an acrylic resin with a liquid that contains, as the essential ingredients, the specific fluoro(meth)acrylate and a polyfunctional (meth)acrylate, the mean particle size of the acrylic resin powder is not particularly limited, but may also preferably have any of the above-noted sizes.

As mentioned above, the compatibility between the acrylic resin and the fluoro(meth)acrylate in the composition of the invention may have significant influences on the handlability of the composition. The compatibility between the two is preferably evaluated by measuring the viscosity of the solution to be prepared by dissolving the acrylic resin in the fluoro(meth)acrylate. For obtaining compositions capable of being handled with ease, it is preferable that the resin solution prepared by dissolving an acrylic resin in the monomer component to have a resin concentration of 5% by weight has a viscosity of at least 100 cps at 25° C., and the acrylic resin that satisfies the requirement is used in preparing the composition of the invention. If an acrylic resin of which the solution in the monomer component in that condition is smaller than 100 cps is in the composition, the polymerized and cured composition may be less tough.

Preferred examples of the fluoro(meth)acrylate of formula (I) for use in the denture rebase of the invention include 1H,1H,2H,2H-nonylfluorohexyl (meth)acrylate, 1H,1H,2H,2H-tridecafluorooctyl (meth)acrylate, 1H,1H,2H,3H,3H-2-hydroxy-tridecafluorononyl (meth)acry late, 1H,1H,2H,2H-undecafluoro-5-methylhexyl (meth)acry late, 1H,1H,5H-octafluoropentyl (meth)acrylate, 1H,1H,6H-decafluorohexyl (meth)acrylate, 1H,1H,7H-dodecafluoroheptyl (meth)acrylate, 1H,1H,9H-hexadecafluorononyl (meth)acrylate, 1H,1H,3H-hexafluorobutyl (meth)acrylate, 1H,1H,2H,2H,7H-decafluoroheptyl (meth)acrylate, 1H,1H,2H,4H,7H-decafluoroheptyl methacrylate, etc.

Of the fluoro(meth)acrylates, more preferred are four, 1H,1H,3H-hexafluorobutyl methacrylate, 1H,1H,5H-octafluoropentyl methacrylate, 1H,1lH,6H-decafluorohexyl methacrylate and 1H,1H,7H-dodecafluoroheptyl methacrylate. Of the four, even more preferred are two, 1H,1H,6H-decafluorohexyl methacrylate and 1H,1H,7H-dodecafluoroheptyl methacrylate. The denture rebases that contain one or more selected from those compounds are better than the others containing any other fluoro(meth) acrylates, since they are hardly discolored and stained, and hardly absorb water and odorous substances, and since they do not irritate the oral mucous membrane.

Preferred examples of the polyfunctional (meth)acrylate (c) for use in the denture rebase of the invention include alkylene glycol di(meth)acrylates such as ethylene glycol di(meth)acrylate, 1,3-propanediol di(meth)acrylate, 1,4-butanediol di(meth)acrylate, 1,5-pentanediol di(meth) acrylate, 1,6-hexanediol di(meth)acrylate, 1,7-heptanediol di(meth)acrylate, 1,8-octanediol di(meth)acrylate, 1,9-nonanediol di(meth)acrylate, 1,10-decanediol di(meth) acrylate, 1,11-undecanediol di(meth)acrylate, 1,12-dodecanediol di(meth)acrylate, 1,13-tridecanediol di(meth) acrylate, 1,14-tetradecanediol di(meth)acrylate, 1,15-pentadecanediol di(meth)acrylate, 1,16-hexadecanediol di(meth)acrylate, 1,17-heptadecanediol di(meth)acrylate, 1,18-octadecanediol di(meth)acrylate, 1,19-nonadecanediol di(meth)acrylate, 1,20-eicosanediol di(meth)acrylate, neopentyl glycol di(meth)acrylate, etc.; polyalkylene glycol di(meth)acrylates such as diethylene glycol di(meth) acrylate, triethylene glycol di(meth) acrylate, dipropylene glycol di(meth)acrylate, polyethylene glycol di(meth) acrylate, etc.; as well as glycerin di(meth) acrylate, 2,2'-bis{p-($\gamma$-methacryloxy-$\beta$-hydroxypropoxy)phenyl}propane, bisphenol A di(meth)acrylate, 2,2'-di(4-methacryloxypolyethoxyphenyl)propane (preferably having from 2 to 10 ethoxy groups in one molecule), 1,2-bis(3-methacryloxy-2hydroxypropoxy) butane, trimethylolpropane tri(meth)acrylate, pentaerythritol tetra(meth)acrylate, urethane (meth)acrylate, etc. One or more these (meth) acrylate monomers may be in the composition, either singly or as combined.

Of the polyfinctional (meth)acrylates mentioned above, especially preferred are alkylene glycol di(meth) acrylates in which the alkylene group between the two (meth)acryloyl groups has from 3 to 20 carbon atoms. In these, the alkylene group may be linear, branched or cyclic. The compositions containing one or more of these compounds are better than the others containing any other polyfunctional (meth) acrylates, since the compounds in them are more effective for preventing the polymerized and cured compositions from absorbing water and from absorbing odorous substances. Another advantage of the monomers of that type which we have found is that adding any of them to the composition of the invention further improves the toughness of the cured composition.

In the denture rebase of the invention, the proportions of the acrylic resin, the fluoro(meth)acrylate and the polyfunctional (meth)acrylate are preferably such that the amount of the acrylic resin (a) independently falls between 25 and 85% by weight, more preferably 35 and 75% by weight, that of the fluoro(meth)acrylate (b) independently falls between 15 and 75% by weight more preferably 20 and 65% by weight, and that of the polyfunctional (meth)acrylate (c) independently falls between 0.1 and 20% by weight, more preferably 2 and 15% by weight.

One preferred embodiment of the composition of the invention includes (a) from 25 to 85% by weight of an acrylic resin having a weight-average molecular weight of from 10,000 to 1,000,000, (b) from 15 to 75% by weight of at least one fluoro(meth)acrylate selected from one or more of 1H,1H,3H-hexafluorobutyl methacrylate, 1H,1H,5H-octafluoropentyl methacrylate, 1H,1H,6H-decafluorohexyl methacrylate and 1H,1H,7H-dodecafluoroheptyl methacrylate, and (c) from 0.1 to 20% by weight of at least one polyfunctional (meth)acrylate selected from one or more of alkylene glycol di(meth)acrylates in which the alkylene group between the two (meth)acryloyl groups has from 3 to 20 carbon atoms (the alkylene group may be linear, branched or cyclic). The preferred composition is especially favorable to denture rebases, since it is easy to handle and since its cured product is tough and exhibits good contamination and staining resistance.

One specific characteristic of the denture rebase of the invention is that the polymerized and cured product of the composition has good contamination and staining resistance. In particular, the denture rebase of the invention is hardly stained with edible dyes, and the amount of water absorbed (water absorption is one reason for offensive smelling of dentures) and that of odorous components to be absorbed by it are much reduced, as compared with any other conventional denture rebases. More concretely, the degree of staining, $\Delta E^*$, of a conventional denture rebase in an aqueous solution of turmeric (curry powder) is at least 40, and the water absorption thereof in the solution is about 15 $\mu g/mm^3$ or so; while, on the other hand, the degree of staining with turmeric, $\Delta E^*$, of the composition of the invention is reduced to lower than the ordinary level, the water absorption thereof is reduced to at most 10 $\mu g/mm^3$, and the methylmercaptan absorption thereof is reduced to about $\frac{2}{3}$ of the level of conventional, commercially-available denture rebases. Within the above contamination and staining resistance ranges, any other polymerizable monofnctional monomers that may copolymerize with the fluoro(meth) acrylate of formula (I) and the polyfinctional (meth)acrylate to be in the composition may be optionally added to the composition.

As the polymerizable monofunctional monomer component, generally preferred are monofunctional (meth) acrylates including methyl (meth)acrylate, ethyl (meth) acrylate, butyl (meth)acrylate, pentyl (meth)acrylate, hexyl (meth)acrylate, 2-ethylhexyl (meth)acrylate, tetrahydrofurfuryl (meth)acrylate, decyl (meth)acrylate, lauryl (meth) acrylate, myristyl (meth)acrylate, stearyl (meth)acrylate, cetyl (meth)acrylate, etc mixtures may be used.

The polymerization initiator in the denture rebase of the invention may be any one known to those of skill in the art, and is not particularly limited. It may be any of photopolymerization initiators and/or thermal polymerization initiators and/or chemical polymerization initiators. The photopolymerization initiators include, for example. combinations of $\alpha$-diketone/reducing agent, ketal/reducing agent, thioxanthone/reducing agent, etc. The $\alpha$-diketone includes, for example, camphorquinone, benzil, 2,3-pentanedione. etc. The ketal includes, for example, benzyl dimethyl ketal, benzyl diethyl ketal, etc. The thioxanthone includes, for example, 2-chlorothioxanthone, 2,4-diethylthioxanthone, etc.

The preferable reducing agent includes, for example, tertiary amines such as 2-(diethylamino)ethyl methacrylate, N,N-bis{(meth)acryloyloxyethyl}-N-methylamine, ethyl 4 dimethylaminobenzoate, butyl 4-dimethylaminobenzoate, butoxyethyl 4-dimethylaminobenzoate, N-methyldiethanolamine, 4-dimethylaminobenzophenone, N,N-di(2-hydroxyethyl)-p-toluidine, dimethylaminophenanthol, etc.; aldehydes such as dimethylaminobenzaldehyde, terephthalaldehyde, etc.; thiol compounds such as 2-mercaptobenzoxazole, decanethiol, 3-mercaptopropyltrimethoxysilane, thiobenzoic acid, etc.

To photopolymerize the composition through UV exposure, favorable are benzoin alkyl ethers, benzyldimethyl ketal, etc. Also preferably used are acylphosphine oxide photopolymerization initiators, which include, for example, 2,4,6-trimethylbenzoyldiphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyldi-(2, 6-dimethylphenyl) phosphonate, 2,4,6-trimethylbenzoylethoxyphenylphosphine oxide, etc. These acylphosphine oxide photopolymerization initiators may be used either singly or as combined with a reducing agent of, for example, various amines, aldehydes, mercaptans, salts of sulfinic acids, etc. One or more of these photopolymerization initiators may be used herein either singly or as combined. The amount of the photopolymerization initiator to be in the denture rebase of the invention may generally fall between 0.001 and 15% by weight, but preferably between 0.1 and 10% by weight of the total (100% by weight) of the denture rebase.

Preferably, the denture rebase of the invention may be in two different package forms when the photopolymerization initiator is used; one being a two-package product composed of a powder package and a liquid package, and the other being a one-package product of a paste. The powder package and the liquid package of the former two-package product are mixed to give a paste before use, and the resulting paste is applied to the oral cavity and polymerized and cured therein. For this, the photopolymerization initiator may be added to any one or both of the powder package and the liquid package. On the other hand, to the one-package product of a paste, the photopolymerization initiator is added to the one-package paste.

Preferably, the thermal polymerization initiator for use in the invention may contain an organic peroxide of, for example, diacyl peroxides, peroxyesters, dialkyl peroxides, peroxyketals, ketone peroxides, hydroperoxides, etc. More preferably, the diacyl peroxides include, for example, benzoyl peroxide, 2,4-dichlorobenzoyl peroxide, m-toluoyl peroxide, etc.

The preferred peroxyesters include, for example, t-butylperoxy benzoate, bis-t-butylperoxy isophthalate, 2,5-dimethyl-2,5-bis(benzoylperoxy)hexane, t-butylperoxy 2-ethylhexanoate, t-butylperoxyisopropyl carbonate, etc.

The preferred dialkyl peroxides include, for example, dicumyl peroxide, di-t-butyl peroxide, lauroyl peroxide, etc.

The preferred peroxy ketals include, for example, 1,1-bis (t-butylperoxy)-3,3,5-trimethylcyclohexane, etc.

The preferred ketone peroxides include, for example, methyl ethyl ketone peroxide. etc.

The preferred hydroperoxides include, for example, t-butylhydroperoxide etc. One or more of these thermal polymerization initiators may be used either singly or as combined. The amount of the oxidizing agent to be in the denture rebase of the invention may generally fall between 0.01 and 15% by weight, but preferably between 0.1 and 10% by weight of the total (100% by weight) of the denture rebase.

Preferably, the denture rebase of the invention may be in two different package forms when the thermal polymerization initiator is used; one being a two-package product composed of a powder package and a liquid package, and the other being a one-package product of a paste. The powder package and the liquid package of the former two-package product are mixed to give a paste before use, and the resulting paste is applied to the oral cavity and polymerized and cured therein. For this, the thermal polymerization initiator may be added to any one or both of the powder package and the liquid package. On the other hand, for one-package product of a paste, the thermal polymerization initiator is added to the one-package paste.

As the chemical polymerization initiator for use herein, preferred are redox polymerization initiators of, for example, a combination of organic peroxide/amine, organic peroxide/amine/sulfinic acid (or its salt), etc. Where such a redox polymerization initiator is used in the denture rebase of the invention, the denture rebase is preferably be divided into at least two parts which are separately wrapped or packaged and which separately contain either one of the oxidizing agent and the reducing agent for the redox polymerization initiator.

To the oxidizing agent of the redox polymerization initiator, the same as those for the thermal polymerization initiator mentioned above could apply. One or more of these oxidizing agents may be used herein either singly or as combined. The amount of the oxidizing agent to be in the denture rebase of the invention may generally fall between 0.01 and 15% by weight, but preferably between 0.1 and 10% by weight of the total (100% by weight) of the denture rebase.

For the reducing agent, preferably used are tertiary amines, which include, for example, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl4-i-propylaniline, N,N-dimethyl-4-t-butylaniline, N,N-dimethyl-3,5-di-t-butylaniline, N,N-di (2-hydroxyethyl)-p-toluidine, N,N-di(2-hydroxyethyl)-3,5-dimethylaniline, N,N-di(2-hydroxyethyl)-3,4-dimethylaniline, N,N-di(2-hydroxyethyl)-4-ethylaniline, N,N-di(2-hydroxyethyl)-4-i-propylaniline, N,N-di(2-hydroxyethyl)-4-t-butylaniline, N,N-di(2-hydroxyethyl)-3, 5-di-i-propylaniline, N,N-di(2-hydroxyethyl)-3,5-di-t-butylaniline, ethyl 4-dimethylaminobenzoate, n-butoxyethyl 4-dimethylaminobenzoate, (2-methacryloyloxy)ethyl 4-dimethylaminobenzoate, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, etc.

One or more of the above reducing agents may be used herein either singly or as combined. The amount of the reducing agent to be in the denture rebase of the invention may generally fall between 0.01 and 15% by weight, but preferably between 0.1 and 10% by weight of the total (100% by weight) of the denture rebase.

Where the denture rebase is in the form of a two-package product composed of a powder package and a liquid package and where it contains a chemical polymerization initiator such as that mentioned above, the oxidizing agent (e.g., peroxides) and the reducing agent (e.g., tertiary amines) in the chemical polymerization initiator are preferably separately added to any of the powder package and the liquid package. Two pastes each separately containing any of the oxidizing agent and the reducing agent are mixed before use so as to polymerize and cure the denture rebase in the oral cavity.

The denture rebase of the invention may optionally contain a filler. The filler may be any of organic or inorganic substances. Preferred inorganic fillers include, for example, silica, silica-based minerals such as kaolin, clay, mica, etc.; and silica-based ceramics and glass additionally containing any of $Al_2O_3$, $B_2O_3$, $TiO_2$, $ZrO_2$, BaO, $La_2O_3$, $SrO_2$, CaO, $P_2O_5$, etc. Especially preferred are lanthanum glass, barium glass, strontium glass, soda glass, lithium borosilicate glass, zinc glass, fluoroaluminium borosilicate glass, borosilicate glass, bioglass, etc. Also preferred are crystalline quartz, hydroxyapatite, alumina, titanium oxide, yttrium oxide, zirconia, calcium phosphate, barium sulfate, aluminium hydroxide, etc.

Also employable herein are inorganic/organic composite fillers, which may be prepared by dispersing an inorganic filler in an organic resin, or by coating an inorganic filler with an organic resin, and even fibrous reinforcing agents. These are to increase the hardness and improve the abrasion resistance of the polymerized and cured composition. The composition for the denture rebase of the invention may further contain any of polymerization inhibitors (e.g., hydroquinone, hydroquinone monomethyl ether, butylhydroxyltoluene, etc.) antioxidants, UV absorbents (e.g., benzophenone), pigments, dyes, fibers for forming mimic blood vessels, etc.

One preferred package form of the denture rebase of the invention is a two-package product composed of an acrylic resin powder package and a monomer liquid package, in which is used, as the polymerization catalyst, a chemical polymerization initiator containing a combination of a peroxide and a reducing agent. The powder/liquid two-package dental rebase product for chemical polymerization has the advantages of good handlability and good dental use. In particular, especially preferred is the two-package product in which the acrylic resin powder package contains a peroxide, and the monomer liquid package that includes the specific fluoro(meth)acrylate and a polyfunctional (meth)acrylate contains a tertiary amine. In dental use, the two packages are mixed to thereby polymerize and cure the resulting blend.

In the denture rebase of the above-identified powder/liquid two package product for chemical polymerization, the polymerization catalyst is more preferably a combination of an organic peroxide and a tertiary amine. As the organic peroxide, for example, preferred is benzoyl peroxide. As the tertiary amine, for example, preferred are aromatic tertiary amines, and more preferred are N,N-dimethylaniline, N,N-dimethyl-p-toluidine, N,N-di(2-hydroxyethyl)aniline, N,N-di(2-hydroxyethyl)-p-toluidine, etc.

Preferably, the acrylic resin powder is of spherical particles having a particle size of from 10 to 100 μm, more preferably 20–90 μm, and most preferably 30–80 μm. Using this is preferred, since the powder is easy to handle and since the paste to be prepared by mixing the powder with a monomer liquid could be well impressed with the surface profile of the oral mucous membrane.

As the acrylic resin powder, especially preferred is a polymer of methyl (meth)acrylate, ethyl (meth)acrylate or butyl (meth)acrylate. The acrylic resin powder of such spherical particles may be obtained through suspension polymerization or the like.

To the powdery ingredient that includes such an acrylic resin powder and a peroxide, preferably added is an inorganic oxide powder of fine particles having a particle size of from 0.001 to 0.1 microns and a specific surface area of from 20 to 500 $m^2/g$, as it significantly improves the fluidity of the resulting powdery ingredient. The powdery ingredient additionally containing such an inorganic oxide powder is easy to handle in dental treatment. Preferably, a dentist will use a metering cup or spoon for metering the powdery ingredient for dental treatment with it. In this step, if the powdery ingredient is poorly fluid or if it adheres onto the wall of the metering container, the dentist will have difficulty in metering it. The fluidity of the acrylic resin powder alone is often poor. The present inventors have found that adding a small amount of such fine inorganic oxide particles to the acrylic resin powder significantly improves the fluidity of the resulting powder mixture.

Fine inorganic oxide particles usable for that purpose may be of silica, alumina, titanium oxide, zirconia or the like. Of those, especially preferred is silica having high dispersibility, such as typically Aerosil (trade name). The amount of the fine inorganic oxide powder that may be added to the acrylic resin powder may generally fall between 0.01 and 5% by weight, but preferably between 0.05 and 1% by weight of the acrylic resin powder.

One especially preferred embodiment of using the two-package denture rebase in dental treatment is mentioned. The acrylic resin powder ingredient containing a peroxide and the monomer liquid ingredient containing a tertiary amine are separately metered in consideration of the curing time for the composition, and mixed together. After the acrylic resin powder has been dissolved in the liquid ingredient in some degree to give a soft and thick paste, the resulting paste is piled up on the oral mucous membrane-facing surface of the denture to be rebased. The denture with the paste thus being piled up on its surface is then set in the oral cavity of the patient, and the upper and lower teeth of the patient are made to occlude in that condition and kept as such for a few minutes to ten and a few minutes, thereby making the paste polymerized and cured to be a rebase on the denture between the occluding upper and lower teeth. To improve the adhesiveness between the rebase of the invention and the oral mucous membrane-facing surface of the denture to be rebased with it, an adhesive primer may be first applied onto the surface of the denture. After the rebase on the denture has been thus cured, the denture is taken out of the oral cavity of the patient. The rebase is trimmed to remove edges that protrude from the oral mucous membrane-facing surface of the denture, and is optionally polished. In that manner, rebasing the denture with the rebase of the invention is finished.

EXAMPLES

Having generally described this invention, a further understanding can be obtained by reference to certain specific examples which are provided herein for purposes of illustration only and are not intended to be limiting unless otherwise specified.

The meanings of the abbreviations used in the following Examples and Comparative Examples are mentioned below.

| | |
|---|---|
| 6FMA: | 1H,1H,3H-hexafluorobutyl methacrylate |
| 5F/4H-BMA: | 1H,1H,2H,2H-pentafluorobutyl methacrylate |
| 8FMA: | 1H,1H,5H-octafluoropentyl methacrylate |
| 10FMA: | 1H,1H,6H-decafluorohexyl methacrylate |
| 12FMA: | 1H,1H,7H-dodecafluoroheptyl methacrylate |
| 16FMA: | 1H,1H,9H-hexadecafluorononyl methacrylate |
| 5FMA: | 2,2,3,3,3-pentafluoropropyl methacrylate |
| 19FMA: | 1H,1H,2H,2H-nonadecafluoroundecyl methacrylate |
| 7F/12H-NMA: | 7,7,8,8,8-pentafluorononyl methacrylate |
| α-FMA: | α-fluoromethyl acrylate |
| BMA: | butyl methacrylate |
| NMA: | nonyl methacrylate |
| EHMA: | 2-ethylhexyl methacrylate |
| PMMA: | polymethyl methacrylate |
| PEMA: | polyethyl methacrylate |
| PBMA: | polybutyl methacrylate |

-continued

| | |
|---|---|
| 1,6-HD: | 1,6-hexanediol dimethacrylate |
| 1,10-DD: | 1,10-decanediol dimethacrylate |
| 3G: | triethylene glycol dimethacrylate |
| TMDPO: | 2,4,6-trimethylbenzoyldiphenylphosphine oxide |
| BPO: | benzoyl peroxide |
| DMPT: | N,N-dimethyl-p-toluidine |
| DEPT: | N,N-dihydroxyethyl-p-toluidine |

The samples prepared in Examples and Comparative Examples were tested according to the following test methods.

(1) Test of staining polymerized and cured products with edible dye:

The samples were tested according to the method described in a reference, Takamata's report in the Journal of Nippon Prosthodontics Society, Vol. 35, No. 3, pp. 542–555 (1991), the entire contents of which are hereby incorporated by reference. Briefly, a pasty composition was filled in a disc mold capable of forming discs having a thickness of 1 mm and a diameter of 2 cm and cured therein. The cured disc was immersed in an aqueous solution of 0.05 wt. % turmeric at 37° C. for 7 days. Before and after immersed, the change in the color of the disc was measured with a calorimeter (from Nippon Denshoku). The color change is represented by $\Delta E^*$. Thus measured before and after immersed in the aqueous turmeric solution, the chromaticity of the disc was plotted as the chromaticity coordinates in the L*a*b* chromaticity diagram stipulated in JIS-Z-8729. in which the distances between the two points plotted indicates $\Delta E^*$. Concretely, the color change, $\Delta E^*$ is represented by the following equation:

$$\Delta E^* = \{(L_1^* - L_2^*)^2 + (a_1^* - a_2^*)^2 + (b_1^* - b_2^*)^2\}^{1/2}$$

wherein $(L_2^*, a_2^*, b_2^*)$ indicate the chromaticity coordinates of the non-immersed disc and $(L_2^*, a_2^*, b_2^*)$ indicate those of the immersed disc. To measure its data, the disc was placed in front of a standard neutral sheet for chromaticity measurement. Larger values of $\Delta E^*$ indicate that the samples tested were stained to a higher degree.

(2) Test of polymerized and cured products for odor absorption:

A pasty composition was filled in a disc mold capable of forming discs having a thickness of 1 mm and a diameter of 2 cm, and cured therein. The cured disc was immersed in 10 ml of an aqueous solution of 0.5 wt. % methylmercaptan at 37° C. for 24 hours, then washed with water, and dried. The amount of methylmercaptan released by the disc for the first 1 hour was measured. To measure it, the disc was put in a laboratory glass tube (100 ml); and kept therein at 25° C. for 1 hour, and the methylmercaptan concentration in the tube was measured with a methylmercaptan gas detector tube (suction capacity: 100 ml). From the length of the detector tube of which the color changed, obtained was the amount of methylmercaptan released by the disc.

(3) Test of polymerized and cured products for water absorption and dissolution:

The samples were tested according to the method described in ISO 1567. Briefly, a pasty composition was filled in a disc mold capable of forming discs having a thickness of 1 mm and a diameter of 2 cm, and cured therein. The cured disc was put into a desiccator having dry silica gel therein, and dried therein at 37±1° C. for 23 hours and then at 25±1° C. for 1 hour, and the dried disc was weighed. This was repeated until the weight of the disc measured became constant (mass of disc, WI). After its weight became constant, the disc was immersed in water at 37±1° C. for 7 days, and then again weighed (mass of disc. W2). Next, the disc was dried at 37±1° C. for 23 hours and then at 25±1° C. for 1 hour, and weighed. This was repeated until the weight of the disc measured became constant (mass of disc, W3).

Water absorption $(\mu g/mm^3) = (W2 - W3)/V$,

Dissolution in water $(\mu g/mm^3) = (W1 - W3)/V$, wherein V indicates the volume of the disc ($mm^3$).

(4) Test of polymerized and cured products for fracture toughness:

The samples were tested according to the method described in a reference, Matsumoto's report in *Dental Materials and Appliances*, Vol. 7, No. 5, pp. 756–768 (1988), the entire contents of which are hereby incorporated by reference. Briefly, a pasty composition was filled in a mold capable of forming pillars having a size of 2.5×5×30 mm and having a 2.5 mm notch at its center, and polymerized and cured therein with the paste being covered with a glass plate. The cured pillar was tested for its fracture toughness. To measure it, the pillar sample was first polished with waterproof abrasive paper of #1500, then stored in water at 37° C. for 24 hours, and thereafter set in an Instron universal tester. Under the condition, the sample was tested at room temperature and at a cross head speed of 1 mm/min, with the distance between the supports being 20 mm. The point at which the sample was broken indicates the fracture toughness of the sample.

Condition for curing compositions:

Depending on the catalyst formulation therein, the rebase compositions are polymerized in different polymerization modes. The polymerization conditions for different polymerization modes are mentioned below.

Chemical polymerization: in water at 37° C. for 10 minutes.

Photopolymerization: exposed to a lamp for dental fabrication (Morita's α-Light). for 5 minutes.

Thermal polymerization: in water at 100° C. for 1 hour.

Example 1 (powder/liquid two-package composition for chemical polymerization):

A powder ingredient containing 60 g of PMMA (molecular weight, 200,000; mean particle size, 20 μm; solution viscosity, 305 cps), 2 g of BPO, and 0.03 g of fine silica (Nippon Aerosil's trade name, Aerosil 130; specific surface area, 130 $m^2/g$; particle size 0.016 microns) was mixed with a liquid ingredient containing 30 g of 6FMA, 10 g of 1,10-DD and 2 g of DMPT, and polymerized through chemical polymerization to give a cured product. The cured product was subjected to the staining test, the smelling substance-absorbing test, the water absorption and dissolution test, and the fracture toughness test, and the data obtained are given in Table 1. The solution viscosity of polymer as referred to herein is meant to indicate the viscosity of a 5 wt. % polymer solution at 25° C., and the polymer solution is prepared by dissolving the polymer in the fluoromonomer (this is to be in the composition) to have a polymer concentration of 5% by weight. Therefore, in the following Examples, the solution viscosity of one and the same polymer shall vary when the fluoromonomer in which the polymer is dissolved to give its solution varies.

Examples 2 to 6

Samples were prepared in the same manner as in Example 1, except that 8FMA (solution viscosity, 315 cps), 10FMA (solution viscosity, 326 cps), 12FMA (solution viscosity, 370 cps), 16FMA (solution viscosity, 410 cps) or 5F/4H-BMA (solution viscosity, 300 cps) was used in place of 6FMA, and tested in the same manner as therein. The data obtained are given in Table 1.

Comparative Examples 1 to 6

Samples were prepared in the same manner as in Example 1, except that 5FMA. 19FMA, BMA, 7F/12H-NMA, NMA or α-FMA was used in place of 6FMA, and tested in the same manner as therein. The data obtained are given in Table 1. 5FMA is a fluorine-containing monomer, but $R^2$+Rf in its side chain has 3 carbon atoms. 19FMA is a fluoromethacrylate monomer like in Example 1, but $R^2$+Rf in its side chain has 11 carbon atoms. In 7F/12H-NMA, $R^2$+Rf in its side chain has 9 carbon atoms, but the ratio of the fluorine atoms to the other atoms bonding to the carbon atoms constituting $R^2$+Rf is small. BMA and NMA are both methacrylate monomers not containing a fluorine atom. α-FMA has one fluorine atom in the molecule, but its side chain is a methyl group. Therefore, α-FMA differs from the fluoro(meth)acrylate of formula (I) defined in the invention. Example 7:

A powder ingredient containing 60 g of PMMA (molecular weight, 200,000; mean particle size, 20 μm) and 2 g of BPO was mixed with a liquid ingredient containing 30 g of 16FMA, 10 g of 3G and 2 g of DMPT, and polymerized through chemical polymerization to give a cured product. (The polymer solution viscosity was 390 cps.)

Comparative Example 7

A powder ingredient containing 60 g of PMMA (molecular weight, 200,000; mean particle size, 20 [μm; solution viscosity, 290 cps) and 2 g of BPO was mixed with a liquid ingredient containing 30 g of 5FMA, 10 g of 3G and 2 g of DMPT, and polymerized through chemical polymerization to give a cured product. In this composition, the fluoro(meth)acrylate in the liquid ingredient is 5FMA in which $R^2$+Rf in the side chain has 3 carbon atoms.

Comparative Example 8

A powder ingredient containing 60 g of PMMA (molecular weight, 200,000; mean particle size, 20 μm; solution viscosity, 420 cps) and 2 g of BPO was mixed with a liquid ingredient containing 30 g of 19FMA, 10 g of 3G and 2 g of DMPT, and polymerized through chemical polymerization to give a cured product. In this composition, the fluoro(meth)acrylate in the liquid ingredient is 19FMA in which $R^2$+Rf in the side chain has 11 carbon atoms.

Comparative Example 9

A powder ingredient containing 60 g of PMMA (molecular weight, 200,000; mean particle size, 20 μm; solution viscosity, 350 cps) and 2 g of BPO was mixed with a liquid ingredient containing 30 g of EHMA, 10 g of 3G and 2 g of DMPT, and polymerized through chemical polymerization to give a cured product. This composition does not contain a fluoro(meth)acrylate in its liquid ingredient.

TABLE 1

| | Fluoromethacrylate | Solution viscosity (cps) | Polyfunctional methacrylate | Staining (with turmeric); ΔE* | Methylmercaptan concentration (ppm) | Water absorption; μg/mm³ | Dissolution; μg/mm³ | Fracture toughness; MPa m$^{1/2}$ |
|---|---|---|---|---|---|---|---|---|
| Example 1 | 6FMA | 305 | 1,10-DD | 9.8 | 14 | 3.0 | 1.0 | 1.09 |
| Example 2 | 8FMA | 315 | 1,10-DD | 8.3 | 14 | 2.9 | 0.6 | 1.15 |
| Example 3 | 10FMA | 326 | 1,10-DD | 7.0 | 11 | 1.8 | 0.2 | 1.18 |
| Example 4 | 12FMA | 370 | 1,10-DD | 6.8 | 10 | 1.9 | 0.5 | 1.01 |
| Example 5 | 16FMA | 410 | 1,10-DD | 5.6 | 13 | 3.2 | 0.4 | 0.92 |
| Example 6 | 5F/4H-BMA | 300 | 1,10-DD | 15.3 | 16 | 4.2 | 1.1 | 1.08 |
| Comp. Ex. 1 | 5FMA | 290 | 1,10-DD | 16.2 | 20 | 7.7 | 1.5 | 0.91 |
| Comp. Ex. 2 | 19FMA | 420 | 1,10-DD | 6.8 | 18 | 5.0 | 1.0 | 0.60 |
| Comp. Ex. 3 | 7F/12H-NMA | 380 | 1,10-DD | 28.1 | 24 | 4.2 | 0.9 | 0.98 |
| Comp. Ex. 4 | BMA | 267 | 1,10-DD | 43.7 | 23 | 5.9 | 1.5 | 1.01 |
| Comp. Ex. 5 | NMA | 377 | 1,10-DD | 46.2 | 28 | 6.2 | 1.3 | 0.92 |
| Comp. Ex. 6 | α-FMA | 120 | 1,10-DD | 38.0 | 26 | 3.2 | 0.9 | 0.76 |
| Example 7 | 16FMA | 390 | 3G | 12.9 | 18 | 4.1 | 0.9 | 0.91 |
| Comp. Ex. 7 | 5FMA | 290 | 3G | 20.4 | 20 | 7.9 | 2.1 | 0.69 |
| Comp. Ex. 8 | 19FMA | 420 | 3G | 13.8 | 19 | 4.1 | 0.9 | 0.61 |
| Comp. Ex. 9 | none (EHMA) | 350 | 3G | 42.9 | 26 | 10.4 | 3.9 | 1.08 |

Comparative Example 10

A powder ingredient containing 60 g of PMMA (molecular weight, 200,000; mean particle size, 20 μm; solution viscosity, 390 cps) and 2 g of BPO was mixed with a liquid ingredient containing 40 g of 16FMA and 2 g of DMPT, and polymerized through chemical polymerization to give a cured product. The product was evaluated in the same manner as hereinabove, and its data are given in Table 2.

This composition contains a fluoro(meth)acrylate alone but not a polyfunctional (meth)acrylate in the liquid ingredient.

Examples 8 to 14, Comparative Examples 11 and 12

Herein used was the same powder ingredient as in Comparative Example 10. The powder ingredient was mixed with a liquid ingredient in which the monomers were 1,10-DD as the polyfunctional methacrylate and 6FMA as the fluoromethacrylate and these were in the ratio as indicated in Table 2. Each composition was cured in the same manner as hereinabove to give a cured product, which was evaluated also in the same manner. The data obtained are given in Table 2.

TABLE 2

|  | Fluoro-meth-acrylate | Amount of fluoro-methacrylate (g) | Amount of polyfunctional methacrylate, DD (g) | Amount of acrylic resin (g) | Staining (with turmeric) ΔE* | Methylmercaptan concentration (ppm) | Water absorption; μg/mm$^3$ | Dissolution; μg/mm$^3$ | Fracture toughness, MPa · m$^{1/2}$ |
|---|---|---|---|---|---|---|---|---|---|
| Comp. Ex. 10 | 16FMA | 40 | 0 | 60(PMMA) | 14.5 | 22 | 8.9 | 2.7 | 0.89 |
| Comp. Ex. 11 | 6FMA | 40 | 0 | 60(PMMA) | 19.6 | 24 | 9.0 | 2.6 | 0.71 |
| Example 8 | 6FMA | 39.9 | 0.1 | 60(PMMA) | 12.1 | 18 | 5.3 | 1.3 | 1.03 |
| Example 9 | 6FMA | 35 | 5 | 60(PMMA) | 8.5 | 12 | 3.9 | 0.8 | 1.10 |
| Example 10 | 6FMA | 30 | 10 | 60(PMMA) | 7.6 | 14 | 3.1 | 0.8 | 1.08 |
| Example 11 | 6FMA | 25 | 15 | 60(PMMA) | 10.2 | 16 | 4.1 | 0.4 | 1.26 |
| Example 12 | 6FMA | 20 | 20 | 60(PMMA) | 16.6 | 16 | 3.5 | 1.0 | 1.17 |
| Example 13 | 6FMA | 20 | 30 | 50(PMMA) | 35.7 | 18 | 3.8 | 0.7 | 1.20 |
| Example 14 | 6FMA | 10 | 30 | 60(PMMA) | 21.5 | 17 | 4.0 | 0.9 | 1.13 |
| Comp. Ex. 12 | 6FMA | 0 | 40 | 60(PMMA) | 41.5 | 15 | 3.2 | 0.3 | 1.23 |

Example 15 (powder/liquid two-package composition for chemical polymerization):

A powder ingredient containing 60 g of PEMA (molecular weight, 250,000: mean particle size, 60 μm; solution viscosity, 617 cps) and 2 g of BPO was mixed with a liquid ingredient containing 30 g of 6FMA, 10 g of 3G and 2 g of DMPT, and polymerized through chemical polymerization to give a cured product. The product was evaluated in the same manner as hereinabove, and its data are given in Table 3.

Example 16 (powder/liquid two-package composition for chemical polymerization)

A powder ingredient containing 60 g of PEMA (molecular weight, 250,000; mean particle size, 60 μm; solution viscosity, 617 cps) and 2 g of BPO was mixed with a liquid ingredient containing 30 g of 8FMA, 10 g of 3G and 2 g of DEPT, and polymerized through chemical polymerization to give a cured product.

Example 17 (powder/liquid two-package composition for chemical polymerization)

A powder ingredient containing 65 g of PMMA/PEMA copolymer (molecular weight, 700,000; mean particle size, 60 μm; copolymerization ratio, 50/50; solution viscosity, 284 cps) and 2 g of BPO was mixed with a liquid ingredient containing 25 g of 6FMA, 10 g of 1,10-DD and 2 g of DMPT, and polymerized through chemical polymerization to give a cured product.

Example 18 (powder/liquid two-package composition for chemical polymerization)

A powder ingredient containing 60 g of PMMA/PEMA copolymer (molecular weight, 700,000; mean particle size, 60 μm; copolymerization ratio, 50/50; solution viscosity, 284 cps) and 2 g of BPO was mixed with a liquid ingredient containing 25 g of 6FMA, 10 g of 1,10-DD, 5 g of EHMA and 2 g of DEPT, and polymerized through chemical polymerization to give a cured product.

Example 19 (powder/liquid two-package composition for thermal polymerization)

A powder ingredient containing 65 g of PMMA/PEMA copolymer (molecular weight. 700,000; mean particle size, 60 μm; copolymerization ratio, 50/50; solution viscosity, 284 cps) and 2 g of BPO was mixed with a liquid ingredient containing 25 g of 6FMA and 10 g of 1,6-HD, and polymerized through thermal polymerization to give a cured product.

Example 20 (paste/paste two-package composition for chemical polymerization)

Paste A containing 65 g of PMMA/PEMA copolymer (molecular weight, 700,000; mean particle size, 60 μm; copolymerization ratio, 50/50; solution viscosity, 284 cps), 25 g of 6FMA, 10 g of 1,6-HD and 2 g of BPO was mixed with paste B containing 65 g of PMMA/PEMA copolymer (molecular weight, 700,000; mean particle size, 60 μm; copolymerization ratio, 50/50; solution viscosity, 284 cps), 25 g of 6FMA, 10 g of 1,6-HD and 2 g of DMPT, and polymerized through chemical polymerization to give a cured product.

Example 21 (paste/paste two-package composition for photo- and chemical polymerization)

Paste A containing 65 g of PMMA/PEMA copolymer (molecular weight, 700,000; mean particle size, 60 μm; copolymerization ratio, 50/50; solution viscosity, 284 cps), 25 g of 6FMA, 10 g of 1,6-HD, 2 g of BPO and 1 g of TMDPO was mixed with paste B containing 65 g of PMMA/PEMA copolymer (molecular weight, 700,000; mean particle size, 60 μm; copolymerization ratio, 50/50; solution viscosity, 284 cps), 25 g of 6FMA, 10 g of 1,6-HD and 2 g of DMPT, and polymerized through photo polymerization to give a cured product.

Example 22 (one-package paste for photo polymerization)

A paste containing 65 g of PMMA/PBMA copolymer (molecular weight, 400,000; mean particle size, 30 μm; copolymerization ratio, 75/25; solution viscosity, 195 cps), 30 g of 6FMA, 5 g of 1,6-HD and 1 g of TMDPO was polymerized through photo polymerization to give a cured product.

Comparative Example 13 (powder/liquid two-package composition for chemical polymerization)

Herein used was a commercially-available, powder/liquid two-package denture rebase, TOKUSO REBASE (from Tokuyama), which was comprised of 65 g of a powder ingredient and 35 g of a liquid ingredient. The two ingredients were mixed together, and polymerized through chemical polymerization to give a cured product. The product was tested in the same manner as hereinabove, and its data are given in Table 3.

Comparative Example 14 (powder/liquid two-package composition for chemical polymerization)

Herein used was a commercially-available, powder/liquid two-package denture rebase, MILD REBARON (from GC), which was comprised of 65 g of a powder ingredient and 35 g of a liquid ingredient. The two ingredients were mixed together, and polymerized through chemical polymerization to give a cured product.

Comparative Example 18

In the same manner as in Example 23, a liquid ingredient containing α-fluoromethyl acrylate (α-FMA) but not 6FMA was prepared. This was mixed with the same powder ingre-

TABLE 3

| | Fluoro-methacrylate | Acrylic resin | Polyfunctional methacrylate | Staining (with turmeric); ΔE* | Methylmercaptan concentration (ppm) | Water absorption; μg/mm$^3$ | Dissolution; μg/mm$^3$ | Fracture toughness; MPa m$^{1/2}$ | Remarks |
|---|---|---|---|---|---|---|---|---|---|
| Example 15 | 6FMA | PEMA | 3G | 8.0 | 14 | 3.9 | 0.9 | 0.96 | |
| Example 16 | 8FMA | PEMA | 3G | 6.4 | 14 | 4.2 | 0.8 | 0.94 | |
| Example 17 | 6FMA | PMMA/PEMA | 1,10-DD | 5.9 | 10 | 1.8 | 0.2 | 1.28 | |
| Example 18 | 6FMA | PMMA/PEMA | 1,10-DD | 6.2 | 11 | 2.1 | 0.3 | 1.24 | |
| Example 19 | 6FMA | PMMA/PEMA | 1,6-HD | 7.2 | 12 | 1.7 | 0.4 | 1.34 | |
| Example 20 | 6FMA | PMMA/PEMA | 1,6-HD | 7.5 | 10 | 2.0 | 0.5 | 1.21 | |
| Example 21 | 6FMA | PMMA/PEMA | 1,6-HD | 6.9 | 12 | 1.4 | 0.6 | 1.39 | |
| Example 22 | 6FMA | PMMA/PBMA | 1,6-HD | 6.4 | 11 | 2.1 | 0.8 | 1.31 | |
| Comp. Ex. 13 | — | — | — | 35.7 | 28 | 12.9 | 2.6 | 1.19 | TOKUSO REBASE |
| Comp. Ex. 14 | — | — | — | 40.1 | 26 | 10.8 | 3.4 | 0.84 | MILD REBARON |

Example 23

A powder ingredient containing 60 g of PMMA (molecular weight, 200,000; mean particle size, 20 μm), 0.6 g of BPO and 0.02 g of colloid silica powder (Aerosil 380 (trade name) from Nippon Aerosil) was mixed with a liquid ingredient containing 35 g of 6FMA, 5 g of 1,10-DD and 0.15 g of DEPT, and the resulting paste was subjected to an oral mucous membrane irritation test.

Precisely, the paste was tested on hamsters, according to the method described in the International Standard, ISO10993-10 for testing dental materials for oral mucous membrane irritation. For blank control, a cotton piece of 1×1 cm containing 0.4 ml of a physiological saline solution was inserted into one intrabuccal cavity of a hamster; and another cotton piece of 1×1 cm containing 0.4 ml of the paste of the composition prepared herein was inserted into the other intrabuccal cavity of the same hamster. In that condition, the two cotton pieces were kept in contact with the oral mucous membrane of the hamster for 10 minutes. Every 1 hour, the cotton pieces in the mouth of the hamster were exchanged for fresh ones, and the test was repeated four times in all. After the test, the sites to which the cotton pieces had been applied were macroscopically checked for red spots, from which the tested sample was judged negative or positive. Five hamsters were used for testing every one type of sample. If irritated by the sample applied thereto, the oral mucous membrane of the hamster tested shall have red spots seen thereon. The sample that gave red spots on the oral mucous membrane of the hamster tested was judged positive in the test. The data obtained are given in Table 4.

Examples 24 to 28, Comparative Examples 15 to 17

In the same manner as in Example 23, liquid ingredients containing any of the methacrylate monomers shown in Table 4 but not 6FMA were prepared. Each liquid ingredient was mixed with the same powder ingredient as in Example 23 to give a paste, and the paste was subjected to the same oral mucous membrane irritation test as above.

dient as in Example 23 to give a paste, and the paste was subjected to the same oral mucous membrane irritation test as above. The data obtained are given in Table 4. The fluoromonomer in the liquid ingredient prepared herein differs from the fluoromonomer defmed for use in the invention.

TABLE 4

| | Fluoromethacrylate | Negative | Positive |
|---|---|---|---|
| Example 23 | 6FMA | 5 | 0 |
| Example 24 | 5F/4H-BMA | 4 | 1 |
| Comp. Ex. 15 | BMA | 0 | 5 |
| Example 25 | 8FMA | 5 | 0 |
| Example 26 | 10FMA | 5 | 0 |
| Example 27 | 12FMA | 5 | 0 |
| Example 28 | 16FMA | 5 | 0 |
| Comp. Ex. 16 | 7F/12H-NMA | 2 | 3 |
| Comp. Ex. 17 | NMA | 1 | 4 |
| Comp. Ex. 18 | α-FMA | 0 | 5 |

The numerals indicate the numbers of hamsters tested.

Example 29

100 g of PEMA powder (from Negami Kogyo; molecular weight, 250,000; mean particle size, 60 μm; solution viscosity, 680 cps), 1 g of BPO, and 0.05 g of fine silica powder (Aerosil 130; specific surface area, 130 m$^2$/g; particle size 0.016 μm) were uniformly mixed in a ball mill to prepare a powder ingredient. The powder ingredient had good fluidity, and, when shaken in a polyethylene container, it did not adhere onto the wall of the container. On the other hand, 86 g of 10FMA, 14 g of 1,10-DD and 0.24 g of DEPT were separately metered, and uniformly dissolved to prepare a liquid ingredient. These were separately packaged to form a powder/liquid two-package rebase for chemical polymerization.

On the other hand, the area of a PMMA denture to be rebased which could not fit in well with the oral cavity was polished with a carborundum point to remove the uppermost layer, and an adhesive primer was applied to the polished area of the denture. The adhesive primer used herein is one attached to a commercially-available denture rebase, TOKUSO REBASE (from Tokuyama), and this contains, as the essential ingredient, dichloromethane. 2.4 g of the powder ingredient having been prepared above and 2.0 ml of the liquid ingredient also having been prepared above were separately metered, and mixed. The resulting soft paste was immediately piled up on the adhesive primer-coated surface of the denture, and the denture was set in the oral cavity of the patient. Immediately, the upper and lower teeth of the patient were made to occlude in that condition and kept as such for a while. This is for impressing the surface profile of the oral mucous membrane of the patient on the rebase.

The upper and lower teeth of the patient were kept to occlude in that condition for 5 minutes, and the rebase was polymerized and cured. Then, the denture with the cured rebase thereon was taken out of the oral cavity of the patient, and the rebase was trimmed to remove its protruding. To reduce the non-polymerized layer still remaining on the surface of the cured rebase, the denture with the cured rebase thereon was dipped in hot water (at about 50° C.) containing sodium sulfite dissolved therein for 5 minutes. The profile of the trimmed part of the rebase was corrected with accuracy, and the surface of the rebase was polished. In that manner, the denture was well rebased with the rebase composition of the invention and the thus-rebased denture could fit in well with the oral cavity of the patient.

The rebased denture was kept in the oral cavity of the patient for 3 weeks, and taken out of it. The rebase was macroscopically checked, and it was discolored or stained little. A small amount of plaque adhered onto a part of the surface of the rebase, but was readily removed through ultrasonic washing with water. The rebase smelled little.

Comparative Example 19

A powder/liquid two-package rebase having the same composition as in Example 29 was prepared herein. In this, however, EHMA but not 10FMA was used. In the same manner as in Example 29, a denture was rebased with the rebase composition prepared herein. The rebased denture was kept in the oral cavity of the patient for 3 weeks, and taken out of it. The rebase was macroscopically checked, and it was significantly yellowed or browned. In addition, the rebase smelled offensive.

As described in detail hereinabove with reference to its preferred embodiments, the denture rebase of the invention includes a fluoro(meth)acrylate having a specific side chain structure and a specific amount of a polyfunctional (meth)acrylate, and it is free from the serious problems with conventional denture rebases that are readily discolored and stained and absorb smelling substances and water. Specifically, the denture rebase of the invention has good contamination and staining resistance, and its cured product is tough. What is more, the rebase composition of the invention does not irritate the oral mucous membrane.

While the invention has been described in detail and with reference to specific embodiments thereof, it will be apparent to one skilled in the art that various changes and modifications can be made therein without departing from the spirit and scope thereof.

This application is based on Japanese application 54847/1999, filed Mar. 3, 1999, the entire contents of which are hereby incorporated by reference.

What is claimed is:

1. A denture rebase, comprising:
(a) an acrylic resin;
(b) a fluoro(meth)acrylate having the formula (I):

$$CH_2=C(R^1)COO—R^2—Rf \qquad (I)$$

wherein $R^1$ represents a hydrogen atom or a methyl group; $R^2$ represents an alkylene group; Rf represents a perfluoro alkyl group; $R^2$+Rf has 4 to 10 carbon atoms in total, and wherein at least 50% of all atoms bonded to said carbon atoms constituting $R^2$+Rf are fluorine atoms;
(c) a polyfunctional (meth)acrylate comprising at least one alkylene glycol di(meth)acrylate wherein the alkylene group is a linear, branched or cyclic alkylene group having 3 to 20 carbon atoms; and
(d) a polymerization initiator.

2. The denture rebase as claimed in claim 1, wherein $R^2$+Rf has 6 to 10 carbon atoms in total.

3. The denture rebase as claimed in claim 1, which comprises 25 to 85% by weight of the acrylic resin (a).

4. The denture rebase as claimed in claim 1, which comprises 15 to 75% by weight of the fluoro(meth)acrylate (b).

5. The denture rebase as claimed in claim 1, which comprises 0.1 to 20% by weight of the polyfunctional (meth)acrylate (c).

6. The denture rebase as claimed in claim 1, which comprises 0.1 to 10% by weight of the polymerization initiator (d).

7. The denture rebase as claimed in claim 1, wherein the fluoro(meth)acrylate (b) is at least one compound selected from the group consisting of 1H,1H,2H,2H-nonylfluorohexyl (meth)acrylate, 1H,1H,2H,2H-tridecafluorooctyl (meth)acrylate, 1H,1H,2H,3H,3H-2-hydroxy-tridecafluorononyl (meth)acrylate, 1H,1H,2H,2H-undecafluoro-5-methylhexyl (meth)acrylate, 1H,1H,5H-octafluoropentyl (meth)acrylate, 1H,1H,6H-decafluorohexyl (meth)acrylate 1H,1H,7H-dodecafluoroheptyl (meth) acrylate, 1H,1H,9H-hexadecafluorononyl (meth)acrylate, 1H,1H,3H-hexafluorobutyl (meth)acrylate, 1H,1H,2H,2H, 7H-decafluoroheptyl (meth)acrylate, and 1H,1H,2H,4H,7H-decafluoroheptyl methacrylate, and mixtures thereof.

8. The denture rebase as claimed in claim 1, wherein the fluoro(meth)acrylate (b) is at least one compound selected from the group consisting of 1H,1H,3H hexafluorobutyl methacrylate, 1H,1H,5H-octafluoropentyl methacrylate, 1H,1H,6H-decafluorohexyl methacrylate and 1H,1H,7H-dodecafluoroheptyl methacrylate, and mixtures thereof.

9. The denture rebase as claimed in claim 1, wherein the polyfunctional (meth)acrylate (c) is at least one compound selected from the group consisting of alkylene glycol di(meth)acrylates, ethylene glycol di(meth)acrylate, 1,3-propanediol di(meth)acrylate, 1,4-butanediol di(meth) acrylate, 1,5-pentanediol di(meth)acrylate, 1,6-hexanediol di(meth)acrylate, 1,7-heptanediol di(meth)acrylate, 1,8-octanediol di(meth)acrylate, 1,9-nonanediol di(meth) acrylate, 1,10-decanediol di(meth)acrylate, 1,11-undecanediol di(meth)acrylate, 1,12-dodecanediol di(meth) acrylate, 1,13-tridecanediol di(meth)acrylate, 1,14-tetradecanediol di(meth)acrylate, 1,15-pentadecanediol di(meth)acrylate, 1,16-hexadecanediol di(meth)acrylate, 1,17-heptadecanediol di(meth)acrylate, 1,18-octadecanediol di(meth)acrylate, 1,19-nonadecanediol di(meth)acrylate, 1,20-eicosanediol di(meth)acrylate, neopentyl glycol di(meth)acrylate and mixtures thereof.

10. The denture rebase as claimed in claim 1, further comprising a fine inorganic oxide powder having a particle size of from 0.001 to 0.1 microns and a specific surface area of from 10 to 500 m²/g.

11. The denture rebase as claimed in claim 1, comprising a cured reaction product of said (a), (b), (c) and (d).

12. The denture rebase as claimed in claim 1, wherein the polymerization initiator (d) is at least one selected from the group consisting of a photopolymerization initiator, thermal polymerization initiator, and a chemical polymerization initiator, and a mixture thereof.

13. The denture rebase as claimed in claim 1, wherein the polymerization initiator (d) comprises a peroxide and a tertiary amine.

14. A method of making the denture rebase as claimed in claim 1, comprising:

combining said (a), (b), (c) and (d).

15. A two-package powder/liquid composition, comprising: a powder package, comprising:

(a) an acrylic resin powder, and (d') a peroxide; and a liquid package, comprising:

(b) a fluoro(meth)acrylate having the formula (1):

$$CH_2=C(R^1)COO-R^2-Rf \quad (1)$$

wherein $R^1$ represents a hydrogen atom or a methyl group; $R^2$ represents an alkylene group; Rf represents a perfluoro alkyl group; $R^1$+Rf has 4 to 10 carbon atoms in total, and wherein at least 50% of all atoms bonded to said carbon atoms constituting $R^2$+Rf are fluorine atoms, (c) a polyfunctional (meth)acrylate comprising at least one alkylene glycol di(meth)acrylate wherein the alkylene group is a linear, branched or cyclic alkylene group having 3 to 20 carbon atoms, and (d") a tertiary amine;

wherein when said (d') and (d") are combined, a polymerization initiator (d), is formed.

16. The two-package powder/liquid composition as claimed in claim 15, wherein the acrylic resin powder comprises spherical particles having a particle size of 10 to 100 microns.

17. The two-package powder/liquid composition as claimed in claim 16, wherein the powder packages further comprises a fine inorganic oxide powder having a particle size of from 0.001 to 0.1 microns and a specific surface area of from 10 to 500 m²/g.

18. A method for making a dental rebase, comprising combining the powder and liquid packages as claimed in claim 16.

19. A method for rebasing a denture, comprising applying to a surface of a denture the denture rebase as claimed in claim 17.

20. A method for rebasing a denture, comprising applying to a surface of said denture a denture rebase, comprising:

(a) an acrylic resin;

(b) a fluoro(meth)acrylate having the formula (I):

$$CH_2=C(R^1)COO-R^2-Rf \quad (I)$$

wherein $R^1$ represents a hydrogen atom or a methyl group; $R^2$ represents an alkylene group; Rf represents a perfluoro alkyl group; $R^2$+Rf has 4 to 10 carbon atoms in total, and wherein at least 50% of all atoms bonded to said carbon atoms constituting $R^2$+Rf are fluorine atoms;

(c) a polyfunctional (meth)acrylate; and (d) a polymerization initiator.

* * * * *